Figure 1:
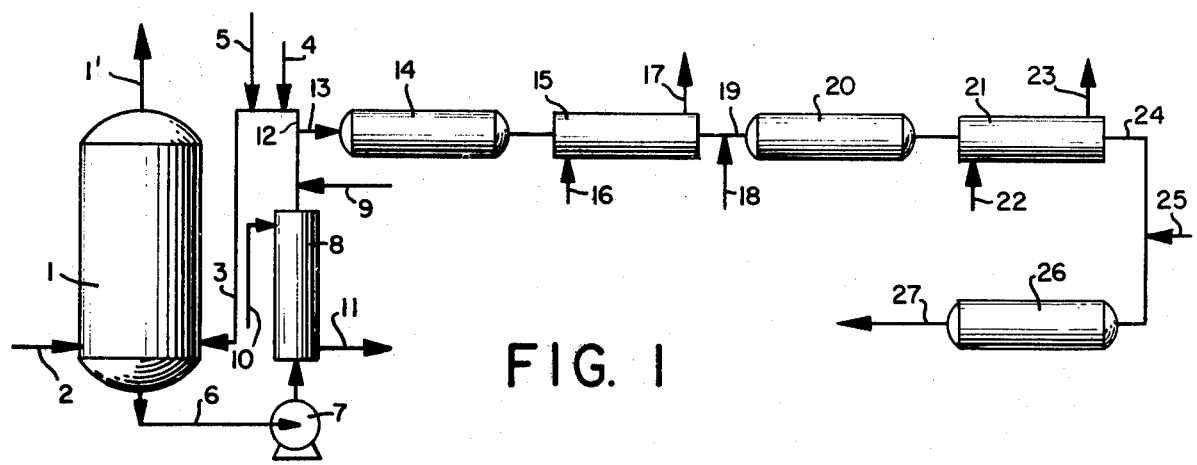

United States Patent [19]

McMullen et al.

[11] 4,314,945

[45] Feb. 9, 1982

[54] ALKYLENE CARBONATE PROCESS

[75] Inventors: Charles H. McMullen, Katonah, N.Y.; James R. Nelson, S. Charleston, W. Va.; Bernard C. Ream, Charleston, W. Va.; Joseph A. Sims, Jr., Elkview, W. Va.

[73] Assignee: Union Carbide Corporation, New York, N.Y.

[21] Appl. No.: 863,354

[22] Filed: Dec. 22, 1977

[51] Int. Cl.³ .................. C07D 317/36; C07D 317/38
[52] U.S. Cl. .................................................. 260/340.2
[58] Field of Search ..................................... 260/340.2

[56] References Cited

U.S. PATENT DOCUMENTS 2,773,070 12/1956 Lichtenwalter et al. ........ 260/340.2
2,773,881 12/1956 Dunn .............................. 260/340.2
3,535,342 10/1970 Emmons ......................... 260/340.2
3,748,345 7/1973 De Pasquale ................... 260/340.2

FOREIGN PATENT DOCUMENTS 38-23175 10/1963 Japan .
170529 5/1965 U.S.S.R. .

OTHER PUBLICATIONS

W. J. Peppel, I & EC, vol. 50, No. 5 (May 1958) pp. 767–770.
H. Springmann, Fette, Sefien, Anstrichmittel, vol. 73, No. 6 (1971) pp. 396–399.

Primary Examiner—Norma S. Milestone
Attorney, Agent, or Firm—Tatsuya Ikeda

[57] ABSTRACT

A process for making alkylene carbonate by the reaction of carbon dioxide and an alkylene oxide of the formula

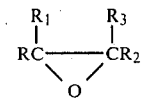

wherein R, $R_1$, $R_2$ and $R_3$ are one or more of hydrogen, alkyl, aryl, alkaryl, aralkyl, cycloalkyl, allyloxy, chloroalkyl, and aryloxy to produce the corresponding carbonate, which comprises:
 (a) providing a homogeneous liquid phase reaction zone in which the predominant material therein is the alkylene carbonate;
 (b) providing a catalytic amount of an alkylene oxide carbonation catalyst to said liquid phase;
 (c) having dissolved in said liquid phase sufficient $CO_2$ to provide a molal amount therein which exceeds the molal amount of the catalyst;
 (d) providing a $CO_2$ pressure in the reaction zone of between about 150 psig and about 750 psig;
 (e) maintaining a sufficient amount of the alkylene oxide in the reaction to maintain the pressure and temperature thereof;
 (f) maintaining the reaction zone at a temperature at which the alkylene oxide and $CO_2$ react to form alkylene carbonate, which temperature is not greater than about 200° C.; and
 (g) correlating the reaction zone temperature and pressure to yield an alkylene carbonate efficiency of at least about 99% and a conversion of at least 99.5%.

13 Claims, 3 Drawing Figures

ALKYLENE CARBONATE PROCESS

The process of this invention allows for the production of alkylene carbonates, in particular ethylene and/or propylene carbonate, under relatively low pressure conditions with exceptional process efficiencies and conversion. In particular, the process of this invention is capable of producing an ethylene carbonate which can be converted to ethylene glycol capable of use in the manufacture of polyester fibers. For example, ethylene carbonate as produced in accordance with this invention, can be simply hydrolyzed to ethylene glycol to produce a product which meets the very straight industry requirements for use in making polyethylene terephthalate fibers.

For a number of years, alkylene carbonates have been commercial products. The main commercial developments are in the manufacture of ethylene carbonate and propylene carbonate. Two companies have been the leaders in the development of commercial processes for the manufacture of alkylene carbonates. The Jefferson Chemical Company, Inc., now a part of Texaco, Inc., put on stream a number of years ago a process for the manufacture of alkylene carbonates. It is believed that that process is characterized by Peppel, "Industrial and Engineering Chemistry", Volume 50, Number 5, May 1958, pages 767–770.

Another developer of a commercial process for the manufacture of alkylene carbonates, in particular ethylene carbonate, has been Chemische Werke Hüls AG, of Marl, West Germany, and its process is believed to be described by Springmann, "Fette Seifen Anstrichmittel", 73 (6), pages 396–399 (1971). According to Springmann, the technology described in the article was utilized to build a plant in Roumania to produce ethylene carbonate.

The literature contains a substantial number of patents and articles which describe processes for producing alkylene carbonates from an alkylene oxide. In particular, reference is made to U.S. Pat. No. 2,773,070, patented Dec. 4, 1956, to Lichtenwalter and Cooper, assigned to Jefferson Chemical Company. That patent describes the reaction of alkylene oxides with carbon dioxide in the presence of certain classes of ammonium halides. Particularly significant is the description in the patent of the use of tetraethylammonium bromide. This particular catalyst is also described by Springmann, supra. The conditions set forth in Lichtenwalter et al., U.S. Pat. No. 2,773,070, comprise temperatures of from 100° to about 225° C., preferably 175° to 215° C., and pressures of more than 300 pounds per square inch gauge. However, the patentees find that the preferable pressure is from about 1000 to about 3000 pounds per square inch gauge. They describe that the process can be carried out batchwise or continuously. In carrying out the reaction, the patentees state that one should use an excess of carbon dioxide over and above the stoichiometric amount required for the reaction with alkylene oxide. This excess may be of the order of from 1% to 500% by weight. They state that an excess of alkylene oxide should be avoided because it results in undesired by-products. These undesired by-products are chiefly alkylene oxide polymers and the ethylene oxide creates something of an explosion hazard. In carrying out the reaction, the patentees state that the amount of catalyst used "in general should be from 0.1 percent to 10 percent, preferably from 1 to 5 percent based on the weight of the reaction mixture". The chief virtue of the catalyst of this patent is that the product alkylene carbonates may be distilled directly from the quaternary ammonium halide catalyst without damage to the product or catalyst. This property of the catalyst renders it particularly suited to continuous operation.

Subsequent to the aforementioned U.S. Pat. No. 2,773,070, the Peppel Article, supra, was issued describing the continuous production of alkylene carbonate utilizing the catalyst of the patent. In characterizing this catalyst, Peppel found that it was remarkably active and its use enabled "virtually quantitative yields of alkylene carbonate to be obtained". Examination of the article shows yield which have been characterized by Springmann, supra, as 95 to 96% of the theory.

The essential difference between the reaction systems described by Peppel and by Springmann, according to Springmann, supra, is that in Peppel's case, the process was provided with product-circulation in the reaction system whereas the process described by Springmann used a plug-flow type of reactor without product-circulation.

In McClellan, U.S. Pat. No. 2,873,282, issued Feb. 10, 1959, assigned to Jefferson Chemical Company, Inc., the catalyst was either a hydroxide, carbonate or bicarbonate of the same category of quaternary ammonium compounds which were mentioned previously in respect to U.S. Pat. No. 2,773,070.

According to Peppel, supra, the reaction which is operated continuously is effected at pressures of 1000 to 1500 psig. The exothermic reaction of ethylene oxide with carbon dioxide is stated by the author to be initiated at about 150° to 175° C. with the catalyst. Because the reaction is rapid, the author states that no side or secondary reactions are involved and the removal of 23 kilocalories per gram mole of heat liberated is the most important consideration governing the setting of a holding time. It is assumed that the author means residence time by the term "holding time".

According to Springmann, supra, the reaction between ethylene oxide and carbon dioxide is fast and can be effected to completion at temperatures between 190° and 200° C. in the presence of the same catalyst which is described by Peppel, supra. He states that a conversion of 96-98% can be obtained in the reactor according to the process that he employed. In the plug-flow reactor employed by Springmann, supra, the reaction pressure is indicated as about 80 atmospheres (1176 psia) and can also be lowered to 65–70 atmospheres (955.5–1029 psia). The article also states that the maximum temperature should not exceed essentially 200° C., otherwise one will have to deal with undesired side-reactions. As the reaction proceeds, the main problem becomes one of removal of liberated heat in quantities of 23 kilocalories per mole. As pointed out in FIG. 2 of Springmann, supra, the temperature rises from the pre-heater to introduction to the main reactor at about 160° to 170° C. and with catalyst injection the reaction proceeds to a temperature which exceeds 200° C., probably in the vicinity of about 225° C. Thereafter, as the reaction runs its course through the reactor, the temperature becomes reduced to the 190°–200° C. level. In order to remove heat of reaction, Springmann, supra, withdraws the heat by a cooling fluid and a high flow rate was chosen for favorable heat transfer. The author states that if the reaction were to occur under adiabatic conditions, with complete conversion, the total heat generated would have to be absorbed as sensible heat, whereby the temperature of the product would rise over 500° C. The author's process is operated without product circulation in the reaction system and the total yield of the reaction unit is cited to be 92 to 95% of the theory, related to the introduced ethylene oxide.

THE USE OF ETHYLENE CARBONATE TO PRODUCE ETHYLENE GLYCOL

Ethylene glycol can be obtained by the hydrolysis of ethylene carbonate. (See U.S. Pat. No. 3,629,343, patented Dec. 21, 1971 and Pohoryles et al., *Journal of the Chemical Society*, pages 3081–3086 (1960). Ethylene glycol is a very important commercial material. Its two major uses are as an anti-freeze and as a starting material in the manufacture of polyester resins which can be converted to fibers. Each of these major uses requires entirely different specifications for the ethylene glycol. The ethylene glycol which is employed in making polyester fibers is considerably purer than the ethylene glycol which is employed as an anti-freeze material. The typical specifications for polyester grade ethylene glycol are as follows:

| | ETHYLENE GLYCOL - POLYESTER GRADE | | |
|---|---|---|---|
| | | Specification Limits | Method |
| 1 | Diethylene glycol | 0.08% by weight, maximum | ASTM E 202-67 |
| 2 | Acidity | 0.005% by weight, maximum, as acetic acid | ASTM E 202-67 |
| 3 | Iron | 0.07 ppm, maximum | ASTM E 202-67 |
| 4 | Chlorides or halides in general | None by test | See Method A below |
| 5 | Ultraviolet transmittance | Wavelength nm / Transmittance, % minimum <br> 220 / 70 <br> 275 / 90 <br> 350 / 98 | See Method B below |
| 6 | Water | 0.08% by weight, maximum | ASTM E 202-67 |
| 7 | Water solubility | Miscible in all proportions at 25° C. | See method C below |
| 8 | Ash | 0.005 gm per 100 ml, maximum | See method D below |
| 9 | Color | 5 platinum-cobalt, maximum | ASTM E 202-67 |
| 10 | Odor | Mild, practically none | See method E below |
| 11 | Suspended matter | Substantially free | See method F below |
| 12 | Specific gravity | 1.1151 to 1.1156 at 20/20° C. | ASTM E 202-67 |
| 13 | Distillation, 760 mm | Ibp 196° C., minimum Dp 200° C., maximum | ASTM E 202-67 |

METHOD A

CHLORIDES OR HALIDE IN GENERAL (a) Introduce 25 ml of the sample into a 100-ml short-form Nessler tube containing 25 ml of distilled water.
(b) Add 5 drops of c.p. concentrated nitric acid.
(c) Add 2 ml of a 10% aqueous solution of silver nitrate and mix thoroughly.
(d) Examine the solution for cloudiness or turbidity which indicates the presence of 0.2 ppm or more chlorides.

METHOD B

ULTRAVIOLET TRANSMITTANCE (a) Ultraviolet spectrophometer: Beckman Model DK or equivalent as determined by reference calibrations.
(b) Procedure: Fill two clean, matched 1.0-cm silica cells with distilled water and place in the ultraviolet spectrophotometer.
(c) Determine the optimum slit-width for 220, 275, and 350 nanometers.
(d) Using the proper slit-width value, determine the cell correction value at 220, 275, and 350 nanometers.
(e) Replace the water in the sample cell with a portion of the sample.
(f) Determine the percent transmission values at 220, 275 and 350 nm, using the respective optimum slit-width for each wavelength, paragraph c.
(g) Correct the transmission values of the sample, paragraph f, for the cell correction, paragraph d, at 220, 275 and 350 nm by means of the following equation, and report the corrected values.
(h) Calculation $(A \times 100)/B$ = corrected percent transmission A = percent transmission of the sample at a given wavelength, paragraph f.
B = percent transmission of water at the same wavelength, paragraph d NOTE: This method of correction is necessary because percent transmission values are nonlinear.

METHOD C

WATER SOLUBILITY (a) Transfer 25 ml of the sample at 25° C. to a 100 ml glass-stoppered graduate and add 25 ml of distilled water at 25° C., in 5-ml portions, shaking the graduate well after each addition.
(b) Add 25 ml of the sample to 25 ml of distilled water in the same manner. The sample is completely miscible if there is no cloudiness or turbidity at any time.

METHOD D

ASH (a) Measure 50 ml of the sample in a graduate and transfer to a 125 ml platinum dish which has been ignited to constant weight, cooled in a desiccator, and tared to the nearest 0.1 mg.
(b) Heat the dish until the vapors continue to burn after the flame is withdrawn. Protect the combustion from drafts and allow the vapors to burn spontaneously.
(c) Ignite the dish to a dull red heat, allow to cool in a desiccator, and weigh to the nearest 0.1 mg. The increase in weight is residue.
(d) Calculation gm residue × 2 = gm ash per 100 ml of sample.

METHOD E

ODOR (a) Pour a few ml of the sample on a clean filter paper and observe the odor at once.

METHOD F

SUSPENDED MATTER (a) Invert a bottle of the sample and examine by transmitted light.

The ethylene glycol that is of a quality to be employed for anti-freeze purposes is classified as technical grade ethylene glycol.

THE INVENTION

This invention is directed to a process for the manufacture of ethylene carbonate which is of such pure quality that it can be hydrolyzed by a standard hydrolysis procedure (see below) to produce ethylene glycol which meets the specifications of Polyester Grade, as set forth above. Heretofore, the continuous processes described in the prior art for the manufacture of ethylene carbonate produce a product which, it has been determined, cannot be hydrolyzed by a standard hydrolysis procedure to produce ethylene glycol which meets the Polyester Grade specification. For example, samples of ethylene carbonate obtained from Jefferson Chemical Division of Texaco, Inc., and from Chemische Werke Hüls AG, of Marl, Germany, have been hydrolyzed by a standard hydrolysis procedure (see below*), and the ethylene glycol so produced was analyzed to determine whether it could pass the aforementioned polyester grade ethylene glycol specification and compared to ethylene glycol as obtained by the same hydrolysis procedure* of ethylene carbonate produced by the process of this invention. The following table illustrates the results of that evaluation:

| Source of Ethylene Carbonate | Results of Monoethylene Glycol Polyester Grade Specification Analyses |
|---|---|
| 1. Process of this invention | Passed all specification tests. |
| 2. Jefferson Chemical Company | Exceeded ultraviolet transmittance and halides specification limits. |
| 3. Chemische Werke Huls | Exceeded ultraviolet transmittance and halides specification limits. |

*Standard Hydrolysis Procedure For This Invention:
To a 5-gal. stainless steel autoclave, equipped with a stirrer, heating coil, back-pressure regulator, and dry gas meter, was charged 8.8 kg of the ethylene carbonate to be tested and 3.4 kg of distilled water. The autoclave was pressurized to 1,100 ± 100 psig with carbon dioxide and heated to 145° ± 15° C. A solution of 75.0–112.5 g of potassium carbonate in 200.0 g of distilled water was pressured into the autoclave with nitrogen. Reaction conditions were maintained until one hour after carbon dioxide evolution stopped. Crude product weighing 7.7–8.0 kg was transferred to a stainless steel receiver under 10 psig carbon dioxide pressure.
The hydrolysis product was refined in a two-still, semi-continuous system comprised of a final concentrator to remove water and a refining column to produce monoethylene by pasteurization. The refined monoethylene glycol was subjected to polyester-grade specification analysis.

The above Table shows that there are a number of the specifications for Polyester Grade ethylene glycol which the commercial products fail to satisfy. For example, it is readily apparent that there is carried forward a lot of bromide in the commercial products and one must assume that this is derived from the bromine in the catalyst. It is also noted that the ethylene carbonate hydrolysis products possess a large concentration of UV absorbers indicating that the processes tend to generate them. It is believed that the UV absorbers are formed because of the high temperatures used in the reaction to form the carbonate and/or the residence time of the reaction. One or both conditions generate precursors to the ultraviolet absorber formation and create the time needed to form them. The Jefferson and Hüls processes employ sufficiently high pressures to suppress the volatilization of the precursors to the ultraviolet absorbers and thereby insure their presence in the ultimate ethylene carbonate product which is to be hydrolyzed to ethylene glycol. This point will be discussed in greater detail below when comparing those processes for making ethylene carbonate with the process of this invention.

There is described herein a process for the manufacture of higher quality alkylene carbonates, e.g., the manufacture of ethylene carbonate which can be hydrolyzed in a conventional manner to make Polyester Grade ethylene glycol. The process of this invention involves the following:

effecting the reaction of carbon dioxide and an alkylene oxide of the formula

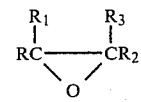

wherein R, $R_1$, $R_2$, and $R_3$ are one or more of hydrogen, alkyl, aryl, alkaryl, aralkyl, cycloalkyl, allyloxy, chloroalkyl, and aryloxy to produce the corresponding carbonate which comprises:

(a) providing a homogeneous liquid phase reaction zone in which the predominant material therein is the alkylene carbonate;

(b) providing a catalytic amount of an alkylene oxide carbonation catalyst (as defined hereinafter) to said liquid phase;

(c) having dissolved in said liquid phase sufficient $CO_2$ to provide a molal amount therein which exceeds the molal amount of the catalyst;

(d) providing a $CO_2$ pressure in the reaction zone of between about 150 psig and about 750 psig;

(e) maintaining a sufficient amount of the alkylene oxide in the reaction to maintain the pressure and temperature thereof;

(f) maintaining the reaction zone at a temperature at which the alkylene oxide and $CO_2$ react to form alkylene carbonate, which temperature is not greater than about 200° C.; and (g) correlating the reaction zone temperature and pressure to yield an alkylene carbonate efficiency of at least about 99% and a conversion of at least about 99.5%.

In carrying out the process of this invention there will be a number of embodiments which are similar and dissimilar to procedures which have been employed by the prior art. There will be other embodiments which are encompassed by or included within ranges broadly set forth in the prior art. Therefore, a careful delineation will be made in the following discussion of these similarities and dissimilarities, and the significance of the disclosed narrower ranges when compared to the broader prior art ranges.

In considering the process of this invention, it is important to take recognition of the variables which are correlated to achieve a certain measure of efficiency for alkylene carbonate production and conversions of alkylene oxide to alkylene carbonate. The concentration of the materials employed in the various steps of the reaction constitute correlations which are predicated upon the impact that each has to effect the aforementioned efficiencies and conversion. Thus, when viewing the provisions of this invention, each step and condition is to be considered in light of their respective correlation in order to achieve such efficiencies and conversions.

As stated in the prior art, the primary material that a reactor will contain in the conversion of the alkylene oxide to alkylene carbonate will be the ultimate product. It will be there as a result of the reaction and also because it is employed as a solvent for the reaction. Such alkylene carbonates are very good solvents and the fact that they do not have to be separated from the product of the reaction simplifies the process considerably. In the practice of this invention it is typical to employ a concentration of the alkylene carbonate of from about 85 to about 99.6 weight percent, based on the weight within the reaction zone. Needless to say, the more alkylene carbonate which is present within the reaction zone also means that less reactants will be present and this of course will determine the temperature of the reaction and, consequently, the reaction rate. More alkylene carbonate present typically results in less reaction and therefore less exotherm. Conversely, less alkylene carbonate present in the reaction zone results in a higher conversion and a greater exotherm. Thus, one can control the reaction conditions within the reaction zone by the amount of alkylene carbonate one has present. Even so, alkylene carbonate concentration has to be correlated with other conditions such as the temperature of the reactants when introduced to the reaction zone, the catalyst concentration, and the ratio of carbon dioxide to ethylene oxide.

As will be more fully explained below, the amount of ethylene carbonate in any one or more of the reaction zones which will constitute the totality of reaction zone entity, as contemplated by this invention, will be predicated to a significant degree upon the type of reactor one employs and/or the types and combinations of reactors that one employs. Each reactor, to the extent it possesses a reaction zone, will provide a component of the total reaction zone.

This invention contemplates the utilization of known catalysts for the conversion of alkylene oxide to alkylene carbonate, as characterized above. Thus, the catalyst may be any one of those which are specifically or more broadly defined by the prior art. However, the most desirable catalysts are those tetraalkylammonium halides which are broadly and specifically defined in U.S. Pat. No. 2,773,070, patented Dec. 4, 1956. The most preferred catalyst is tetraethylammonium bromide. Another catalyst which is particularly preferred is potassium iodide. This catalyst is mentioned in Japanese Pat. No. 6,323,175, issued Oct. 31, 1963.

The catalyst may be employed in amounts ranging from as little as 0.1 to about 3.0 weight percent, based upon the combined weight of the alkylene carbonate, carbon dioxide and alkylene oxide employed in the reaction zone. This point presents an interesting contrast between the process of the instant invention and those described by Peppel, supra, and Springmann, supra. They advocate a lesser amount of catalyst concentration in the reaction. For example, Peppel supra, states that "about 0.25 to 0.5% of catalyst based upon the weight of alkylene oxide and carbon dioxide is ordinarily sufficient to maintain a rapid reaction." And Springmann, supra, states that "the rate of reaction of ethylene carbonate formation is a function of the catalyst concentration; concentrations over 1% by weight related to the introduced ethylene oxide, proved, however, to be disadvantageous, because undesired side reactions, e.g. formation of polymeric products, occur in an increasing degree." [The above quotation from Springmann, supra, is an unofficial translation from the original German text.] The concentration of 1% by weight recited by Springmann, supra, is equivalent to 0.5% of catalyst described by Peppel, supra. However, in the practice of the process of this invention, it has been found that a catalyst concentration of at least 0.5 weight %, and greater, up to 3 weight %, based on the combined weight of alkylene carbonate, alkylene oxide and carbon dioxide provides an attractive rate of reaction coupled with a minimal amount and type of produced impurities. This catalyst concentration is greter than the maximum catalyst concentration described by either of these two references. There is a consequent increase in reaction rate as the catalyst concentration is increased. This increase in rate of reaction by increase in catalyst concentration can be controlled (or diminished) by diluting further with alkylene carbonate and/or by increasing the carbon dioxide to alkylene oxide molar or weight ratio.

Since it is not necessary to apply heat to the reaction [but rather control the exotherm of the reaction so as to keep the temperature within prescribed limits], it is not necessary to rely upon applied temperature to control the reaction temperature. However, that is not outside the bounds of this invention because if there is a need to supply heat to overcome a deficiency of any parameter of the system such as a deficiency in alkylene oxide or catalyst content, it is another variable which is appropriately employable in practising the process of this invention.

As stated previously, the $CO_2$ is dissolved in the homogeneous phase of the reaction zone to provide a molal amount therein which exceeds the molal amount of the catalyst. Molal, as employed, represents the moles of $CO_2$ and catalyst, respectively, per kilogram of the homogeneous liquid phase mixture. Stated otherwise, there must be employed at least one mole of carbon dioxide for each mole of catalyst in the homogeneous liquid phase mixture which comprises the reaction zone. If there is more catalyst than carbon dioxide on a molar basis in the reaction zone, then the amount of undesirable by-products increases even though other processing advantages, which are more fully characterized below, are employed. The undesired by-products include polymer formation and catalyst breakdown. Catalyst breakdown eventually also adversely affects the reaction rate. However, the effect that $CO_2$ concentration is seen to have on impurity formation levels off once the $CO_2$ pressure is at about 400 psig, or above.

The amount of carbon dioxide which is provided in the homogeneous liquid phase reaction mixture comprising the reaction zone may range from about 0.1 to about 6 weight%, based on the weight of the homogeneous liquid phase mixture. There is a correlation between the amount of $CO_2$ and alkylene oxide to achieve a desired reaction rate with a given amount of catalyst. There is also a correlation between the amount of carbon dioxide, alkylene oxide and catalyst supplied to the reaction zone to control the reaction rate. This correlation also impacts upon the temperature and pressure of the reaction. In addition, with more carbon dioxide, there is less likelihood of impurities being formed (i.e., $CO_2$ pressure is at about 400 psig or above).

It is desirable in practicing the process of this invention to employ $CO_2$ pressures in excess of about 400 psig, particularly when the reaction is carried out in a plug-flow type of reactor. The pressure of the reaction zone should be between 150 psig and 750 psig.

These pressure ranges should be contrasted with the pressures which are recited by Lichtenwalter et al., U.S. Pat. No. 2,773,070, Peppel, and Springmann, supra.

As mentioned previously, U.S. Pat. No. 2,773,070 mentions the use of a pressure of more than 300 pounds per square inch gauge. It should be noted that the examples of the patent utilize exceptionally high pressures, with only one example, that is, Example 19, utilizing an initial pressure as low as 580 pounds per square inch followed by heating to 180° C., indicating that the eventual pressure attained in the reaction is considerably above that, probably higher than 900 pounds per square inch gauge. [Compare Example 19 with Example 1 of U.S. Pat. No. 2,773,070, which pressurizes up to 500 pounds per square inch at 40° C. and then seals the reactor and applies heat to 200° C. whereupon the pressure reaches 2250 pounds per square inch gauge]. Therefore, it would seem fair to state that the examples of U.S. Pat. No. 2,773,070 employ, as a minimum pressure, 1200 pounds per square inch gauge. Peppel, supra, states that the reaction "requires use of a vessel able to withstand a working pressure of 1000 to 1500 psig." In Table 1 of Peppel, supra, the reactor pressure is 1500 psig. Springmann, supra, states that the reaction pressure is about 80 atmospheres (1176 psia) and can be lowered, for example, to 65 to 70 atmospheres (955 psia to 1029 psia).

The process temperature of the reaction of this invention is maintained between 100° C. and 200° C. The minimum temperature is that temperature at which the reaction between the alkylene oxide and carbon dioxide will take effect under the catalyzed conditions of the reaction. As pointed out by Springmann, supra, it is desirable to keep the temperature of the reactants below 200° C. As distinctive from Springmann, supra, the process of this invention is desirably carried out so that at no time within the reaction zone does the temperature of the reaction exceed 200° C. It is important to give some consideration to the fact that, as stated earlier, Springmann, supra, discloses the use of a plug-flow reactor where during the course of the reaction the temperature of the reaction exceeds 200° C. to about 225° C. When the reaction at any time during any period of the reaction is allowed to exceed 200° C., it has been determined that there is a considerable increase in the amount of impurities which are formed. These impurities are sufficient to have a deleterious effect on the ability to produce a highly pure alkylene carbonate such as ethylene carbonate which can be hydrolyzed in a conventional manner to produce Polyester Grade ethylene glycol. In considering Peppel, supra, it is noted in Table 1, pages 768, that temperatures are recorded at the top, middle and bottom of the reactor. It is also noted from the schematic illustration of the pilot plant on page 769 that the carbon dioxide is introduced at the bottom of the reactor just below or at about the thermowell (temperature recorder) at the bottom of the reactor. This carbon dioxide, introduced at 40° C., at about the thermowell at the bottom of the reactor, is expected to chill that portion of the reactor contents about the bottom thermowell. If that is true and the temperature, as noted in Table 1 for that thermowell ranges from 185°-197° C. in runs 1-3, the reactor temperature at a point above the bottom thermowell must be greater than that set forth in Table 1. It would appear from an evaluation of the ethylene carbonate obtained from Jefferson Chemical, hydrolyzed according to the standard hydrolysis method characterized above, and analyzed to determine whether the hydrolyzate ethylene glycol met Polyester Grade specification, that the reactor in which the ethylene carbonate is produced is at some point operating above 200° C.

As indicated above, the reaction temperature is governed by a number of process variables, one of which is the heat generated by the reaction. As is typical in such exothermic reactions, the temperature which exists in the reaction zone can be controlled by the amount of each of the reactants which is introduced to the reaction. Thus, by decreasing the amount of alkylene oxide which is present it is possible to reduce the amount of heat generated from the reaction. Moreover, if one reduces the amount of alkylene carbonate present in the reaction zone, the temperature of the reaction will increase. Increasing the concentration of alkylene carbonate in the reaction zone provides a mechanism for decreasing the reaction temperature.

DEFINITION OF THE CATALYST

The catalyst employable in the practice of the process of this invention is a salt which is characterized by the formula

wherein $M^+$ is either an alkali metal cation or a quaternary ammonium cation and $A^-$ is either chloride, bromide or iodide. Illustrative of $M^+$ are the quaternary ammonium cations having the formula:

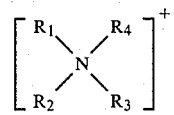

wherein $R_1$, $R_2$, $R_3$, and $R_4$ may each be alkyl, aryl, alkenyl, alkaryl, or aralkyl including substituents thereon in any combination or in which any two or more of the radicals $R_1$, $R_2$, $R_3$, and $R_4$ may be interconnected to form, with the basic nitrogen atom, a heterocyclic such as a pyridine, piperidine, quinuclidine, pyrrolidine, pyrroline, morpholine, thiomorpholine derivatives, or 1,4-diazobicyclo[2.2.2]octane. Preferably, the alkyl group contains from 1 to 20 carbon atoms, the aryl group is phenyl or naphthyl, the alkenyl group contains from 2 to 20 carbon atoms, the alkaryl group is an alkyl substituted phenyl or naphthyl in which the alkyl group contains from 1 to 4 carbon atoms and the aralkyl group is an alkyl group containing from 1 to 4 carbon atoms substituted by a phenyl or naphthyl radical.

As examples of preferred catalysts may be mentioned tetraethylammonium bromide, tetramethylammonium bromide, benzyltriethylammonium bromide, and tetrabutylammonium bromide. These catalysts may easily be produced by heating a tertiary amine with an alkyl bromide. Thus, from triethylamine and benzyl bromide, benzyltriethylammonium bromide is obtained. The quaternary ammonium halide catalysts may be purified by crystallization from a suitable solvent; in most cases an alcohol may be used for this purification. Methyl and ethyl alcohols are satisfactory for this purification in the case of most ammonium halides; however, a preferred solvent for tetraethylammonium bromide is tertiary butyl alcohol in which the catalyst is almost completely insoluble at room temperature, but in which it is quite soluble near the boiling point. Tertiary amyl alcohol is similarly well suited for this use.

Also, illustrative of $M^+$ are the alkali metal ions such as lithium, sodium and potassium. A preferred catalyst is potassium iodide.

In practicing the process of this invention, one may use a mixture of any one or more of the aforementioned catalysts. Thus, the invention contemplates using one or more of the nitrogen-containing catalysts and one or more of the alkali metal-containing catalysts or a combination of one or more of the nitrogen-containing catalysts with one or more of the alkali metal-containing catalysts.

FURTHER DESCRIPTION OF THE PROCESS

Figure 2:
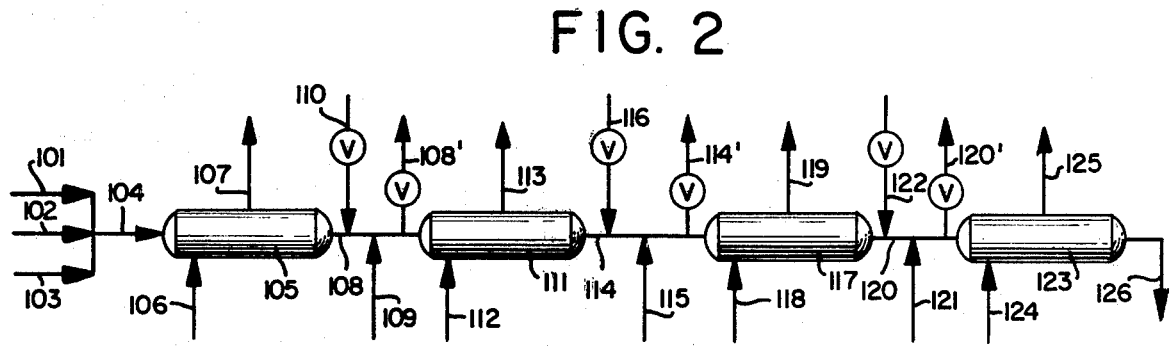
Figure 3:
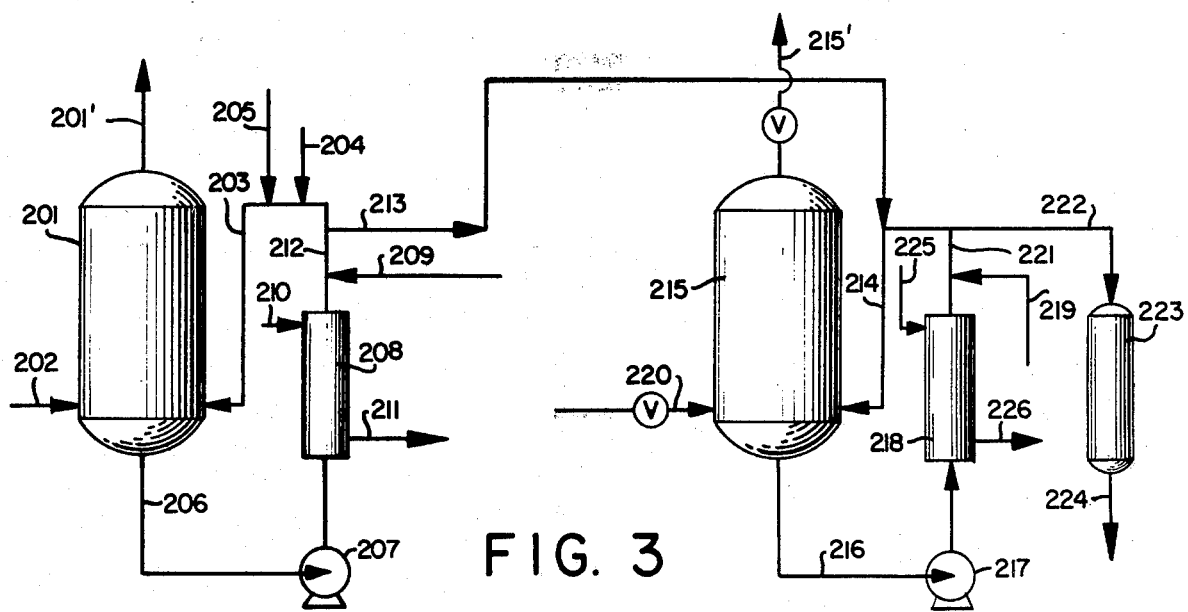

In order to more specifically describe the process of this invention, reference is made to the drawings which depict therein three process variations of the process of this invention in a schematic manner. Referring specifically to FIG. 1, it combines the features of a back-mix reactor in combination with plug-flow reactors. FIG. 2 shows the utilization of a series of plug-flow reactors. FIG. 3 utilizes at least two back mix reactors in series to effectuate the process of this invention. Any one or more combinations of these types of reactors utilizing the principles of the process of this invention may be employed in the practice of this invention. This invention is not intended to be limited by reactor design or type unless specifically stated.

In FIG. 1, a back mix reactor 1 is charged with carbon dioxide through line 2 and with catalyst and alkylene oxide, viz. ethylene oxide, as well as some additional carbon dioxide, if needed, through line 3. Preferably, reactor 1 is a stirred reactor or stirring is effected by the manner in which the gases and liquids are introduced to the interior of the reactor. Stirring ensures good mixing of the material in the interior of the reactor so as to provide maximum and uniform contact of the components as well as give control over temperature within the reactor. A significant point is that back-mix reactor 1 is provided with a vent 1' which allows periodic (i.e., occasionally or continuously) removal of volatile reaction products which have the capability of either undergoing polymerization or additional reactions or, of themselves, forming impurities which will adversely effect the properties of the alkylene carbonate produced. For example, in the case of ethylene carbonate manufactured from ethylene oxide, acetaldehyde is formed and it is a volatile component which can be removed very early from the product stream. However, if left in the product stream too long, it will have sufficient time to undergo further reactions to produce polymeric materials and/or ultraviolet absorbers.

At this point, it is worthwhile to consider the pilot plant reactor depicted by Peppel, supra, on page 769. It is noted that the recirculated reactor is not provided with a vent which would allow the removal of acetaldehyde and as a consequence, acetaldehyde is kept in the liquid medium until the gas-liquid separator, which contains a vent. However, by that time, the acetaldehyde has an opportunity to undergo further reaction and form high boilers and absorbers which, when present in parts-per-million quantities, alter the properties of the ethylene carbonate so that it is incapable of producing Polyester Grade ethylene glycol, when hydrolyzed in the aforementioned conventional manner.

The products of the reaction are removed through line 6 and fed via pump 7 to cooler 8, which is cooled by either water or steam fed through line 10 and recovered from line 11. In a typical case, the temperature is reduced in cooler 8 by approximately 4° to approximately 20° C. and the product stream is removed from cooler 8 by way of line 12, which connects with lines 3 and 13. At this point, additional carbon dioxide can be introduced via line 9. The carbon dioxide can be employed for purposes of temperature control or for make-up of carbon dioxide, or both. A portion of the product stream removed from cooler 8 is fed to line 3 and then into reactor 1, after it is combined with additional alkylene oxide and catalyst. To the product stream recycle fed to line 3, additional ethylene oxide is fed by way of line 4, and the catalyst mixed with the alkylene carbonate (which is employed as reaction solvent) is introduced through line 5. A portion of the stream removed from cooler 8 is taken through line 13 to a plug-flow reactor 14. This reactor is operated under adiabatic temperature and pressure conditions and the effluent from reactor 14 is passed to cooler 15, which is cooled by water or steam fed through line 16, and removed from the cooler via line 17. The effluent from cooler 15 is passed by way of line 19, in which additional or make-up $CO_2$ is added via line 18, to another plug-flow reactor 20. Reactors 20 and 14 can be duplicates. The effluent from reactor 20 is passed to cooler 21, which is similar in construction to cooler 15. Water or steam is fed to the cooler through line 22 and the steam is removed from the cooler by way of line 23. The effluent from cooler 21 is passed by line 24, which has make-up $CO_2$ fed to it through line 25, to another plug-flow reactor 26 of similar size and construction to the previously-mentioned plug-flow reactors. The aforementioned conversions and efficiencies are determined by analysis of the effluent taken from line 27.

With respect to the size of plug-flow reactors 14, 20 and 26 depicted in FIG. 1, they may be chosen to be different or the same. In addition, each of the coolers can be differently sized, and this can be based upon the differences in the sizes of the plug-flow reactors. The carbon dioxide need not be introduced through the lines preceding each of the plug-flow reactors. Indeed, the carbon dioxide may be introduced prior to each of the coolers 8, 15, and 21.

With respect to the apparatus schematically depicted in FIG. 2, the reactants and the catalyst can be introduced through line 104 to plug-flow reactor 105. For example, the catalyst mixed with the alkylene carbonate solvent can be fed to 104 through line 101, the carbon dioxide through line 102 and the alkylene oxide through line 103. The reaction can be initiated by heating reactor 105 with steam fed through line 106 and effluent steam is removed through line 107. To achieve reaction temperature, reactor 105 can be either jacketed or have a combination of heating jacket and tubular heaters placed in its interior or contain only tubular heaters in its interior. On the other hand, it may be desirable to achieve reaction temperature by pre-heating at least one or more of the feed streams to reactor 105. The object is to get the reactants to a temperature which will initiate the reaction, viz. 150° C. to 170° C. Another function of the steam is to also remove heat generated by the reaction when the exotherm of the reaction raises the temperature to one which exceeds the temperature of the steam utilized to initiate the reaction. As a result, the steam then functions as a coolant or heat transfer agent to remove the heat from the reaction zone and thereby exerts control over the reaction to keep the temperature of the reaction zone below 200° C. The effluent from reactor 105 is passed via line 108 to another plug-flow reactor, reactor 111. However, ethylene oxide may be added to the effluent stream via line 109 and $CO_2$ may be optionally added for make up or cooling purposes via line 110. Line 110 possesses a valve for closing that line when it is not desirable to introduce carbon dioxide. Also provided in line 108, is a purge vent, 108', which removes volatiles periodically, i.e., occasionally or continuously, for the reasons stated previously. Line 108' is fitted with a valve for closing or opening the line for venting purposes. After the effluent from reactor 105 has passed through line 108 and it has added to it ethylene oxide, optionally $CO_2$, with or without venting of volatiles, it is fed to plug-flow reactor 111. Plug-flow reactor 111 is either jacketed or possessing internal cooling or heating tubes as described with respect to reactor 105. Water or steam may be fed via line 112 to reactor 111, and effluent steam will be recovered by way of line 113. The choice of using steam or water will be dependent upon the temperature of line 108 effluent which is fed to reactor 111, keeping in mind that the reaction temperature should never exceed 200° C. The effluent from reactor 111 is passed through line 114, which is similarly fitted as was line 108 with a $CO_2$ valved line 116, an alkylene oxide introduction line 115, and a valved vent line, 114' in this case. The effluent is then fed to plug-flow reactor 117, which can be characterized as previously, with respect to reactor 111. Reactor 117 is fitted with water or steam line 118 and steam removal line 119. The procedure is repeated by having the effluent pass through line 120 to reactor 123 which is fitted with water or steam introduction line 124 and steam removal line 125. In line 120, one has the option of feeding $CO_2$ through valved line 122, alkylene oxide through line 121, and venting volatiles through valved line 120'. The effluent from this series of plug-flow reactors is removed and recovered from line 126 and that product satisfies the percent conversion and percent efficiency values that were set forth previously in the characterization of this invention. In considering the use of a series of plug-flow reactors as in FIG. 2, it is not necessary to restrict the number of reactors in series to four. It is possible that one or more additional plug flow reactors can be included in the series to effect the desired percent conversion and percent efficiency and it is also possible that one or more of the plug flow reactors can be removed from the series depending upon the sizing and flow rates as well as temperature control systems that are employed in each plug flow reactor. The object is to achieve the desired percent conversion and percent efficiencies in a temperature controlled system.

FIG. 3 schematically illustrates a process utilizing two back mix reactors in series. In practicing this invention, it is not necessary that only two back mix reactors be employed in the series. It is possible to utilize three or more of them depending on their size, residence times, flow rates, temperatures, and the like considerations. The first of the two back mix reactors in series is reactor 201 which can be a duplicate of reactor 1 of FIG. 1. It contains vent 201' which serves the same function as vent 1' of FIG. 1. $CO_2$ is introduced through line 202 and the reactor effluent is removed via line 206 through pump 207 to cooler 208, water fed through line 210 with steam removal through line 211. Make up carbon dioxide is fed to line 212 via line 209 and the stream is split, part of it being recycled back to reactor 201 through line 203, and the other part being carried by line 213 in line 214 to be fed to back mix reactor 215. Additional alkylene oxide is added to line 203 by way of line 204 and catalyst mixed with alkylene carbonate solvent is introduced through line 205 to line 203. The reactor 215 also contains a vent 215' which can be used to remove volatiles if necessary. However, significant volatiles removal is achieved in reactor 201.

Line 214 contains effluent from reactor 201 plus additional carbon dioxide fed through line 209. In addition it also contains a portion of recycled product obtained from reactor 215 effluent line 216, recirculated by pump 217 to cooler 218 (cooled by water introduced through line 225 with steam removed through line 226) to which is added carbon dioxide make up through line 219 to cooler effluent line 221. The remainder of the effluent not recycled is removed via line 222. In addition, carbon dioxide can be introduced to reactor 215 through valved line 220 for the purposes of make up and/or temperature control. As an optional feature, the effluent from line 222 is fed to a plug flow reactor 223 before final recovery as product stream 224 possessing the percent conversion and the percent efficiency as described previously. If the plug-flow reactor is not needed in this embodiment, then the product stream is obtained from line 222.

This invention has been described in regard to a variety of embodiments thereof. The following represents the best mode regarded for practicing this invention. It is not intended that this invention shall be limited to this best mode and the best mode is only considered exemplary of the various modes which one can employ in practicing the instant invention in accordance with standard chemical and chemical engineering practices.

EXAMPLE

Reference is made to FIG. 1 to assist in characterizing the process assembly or train in which the example is carried out. The following Table I sets forth the line numbers depicted in FIG. 1 and the contents of the streams going through each line. The temperature and pressure of each line is set forth in Table I where appropriate. In regard to coolers 8, 15 and 21, the temperature of the cooling water fed and the steam being removed is specifically stated. Table II supplies the volume or dimensions of the equipment pieces 1, 8, 14, 15, 20, 21, and 26 as set forth in FIG. 1. Also, Table II characterizes the exit temperature of each such piece of equipment. The description above for practicing the process as recited for FIG. 1 is applicable in the carrying out of this example. All reactors are free of any stirrers or other mixer devices. Any mixing which is effected is by the flow of materials into and out of the reactors.

TABLE I

| EXAMPLE DEPICTING MANUFACTURE OF ETHYLENE CARBONATE FROM ETHYLENE OXIDE AND CARBON DIOXIDE | | | | | | | | | | |
|---|---|---|---|---|---|---|---|---|---|---|
| Line Number | 2 | 3 | 4 | 5 | 6 | 1' | 9 | 12 | 13 | 18 |
| Ethylene Oxide - lb.mole/hr | 0 | 7.004 | 1.708 | 0 | 5.442 | .008 | 0 | 5.296 | 0.146 | 0 |

TABLE I-continued
EXAMPLE DEPICTING MANUFACTURE OF ETHYLENE CARBONATE FROM ETHYLENE OXIDE AND CARBON DIOXIDE

| | | | | | | | | | | |
|---|---|---|---|---|---|---|---|---|---|---|
| Carbon Dioxide - lb mole/hr | 1.439 | 2.908 | 0 | 0 | 2.774 | .019 | 0.215 | 2.908 | 0.081 | .030 |
| Ethylene Carbonate - lb mole/hr | 0 | 71.172 | 0 | 0.397 | 72.726 | 0 | 0 | 70.775 | 1.951 | 0 |
| Tetraethylammonium Bromide - lb/hr | 0 | 68.440 | 0 | 1.84 | 68.440 | 0 | 0 | 66.60 | 1.84 | 0 |
| Total - lb/hr | 63.3 | 6772.3 | 75.2 | 36.8 | 6834.4 | 1.2 | 9.5 | 6660.3 | 183.6 | 1.3 |
| Water (steam) - lb/hr | 0 | 0 | 0 | 0 | 0 | 0 | 0 | 0 | 0 | 0 |
| Temperature - °C. | 100 | 179.4 | 20 | 100 | 190.0 | 190.0 | 100 | 181.9 | 181.9 | 100 |
| Pressure - psig | 500 | 500 | 500 | 500 | 500 | 500 | 500 | 500 | 500 | 500 |
| Line Number | 19 | 24 | 25 | 27 | 10 | 11 | 16 | 17 | 22 | 23 |
| Ethylene Oxide - lb mole/hr | 0.115 | 0.048 | 0 | 0.009 | 0 | 0 | 0 | 0 | 0 | 0 |
| Carbon Dioxide - lb mole/hr | 0.080 | 0.091 | 0.078 | 0.052 | 0 | 0 | 0 | 0 | 0 | 0 |
| Ethylene Carbonate - lb/hr | 1.982 | 2.049 | 0 | 2.088 | 0 | 0 | 0 | 0 | 0 | 0 |
| Tetraethylammonium Bromide - lb/hr | 1.84 | 1.84 | 0 | 1.84 | 0 | 0 | 0 | 0 | 0 | 0 |
| Total - lb/hr | 184.9 | 188.3 | 3.4 | 188.3 | 50.1 | 50.1 | 2.9 | 2.9 | 1.7 | 1.7 |
| Water (steam) - lb/hr | 0 | 0 | 0 | 0 | 50.1 | (50.1) | 2.9 | (2.9) | 1.7 | (1.7) |
| Temperature - °C. | 172.2 | 179.4 | 100 | 190 | 110 | 170 | 110 | 160 | 110 | 160 |
| Pressure - psig | 500 | 500 | 500 | 500 | 200 | 165 | 200 | 150 | 200 | 150 |

TABLE II

| Equipment Piece | Volume or Area | Dimensions | Exit Temp. |
|---|---|---|---|
| 1 | Vol. = 1.72 ft$^3$ | Height 2.7 ft, inside diameter 0.9 ft. | 190° C. |
| 8 | Area = 8.88 ft$^2$ | — | 181.9° C. |
| 14 | Vol = .03922 ft$^3$ | 1.8 ft long × 2" ID | 190° C. |
| 20 | Vol = .17798 ft$^3$ | 8.2 ft long × 2" ID | 190° C. |
| 26 | Vol = .3236 ft$^3$ | 14.8 ft long × 2"ID | 190° C. |
| 15 | Area = 0.39 ft$^2$ | — | 172.2° C. |
| 21 | Area = 0.19 ft$^2$ | — | 179.4° C. |

What is claimed is:

1. A process for producing alkylene carbonate by the reaction of carbon dioxide and an alkylene oxide of the formula

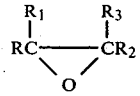

wherein R, R$_1$, R$_2$, and R$_3$ are one or more of hydrogen, alkyl, aryl, alkaryl, aralkyl, cycloalkyl, allyloxy, chloroalkyl, and aryloxy to produce the corresponding alkylene carbonate which comprises:

(a) providing a homogeneous liquid phase reaction zone in which the predominant material therein is the alkylene carbonate, said alkylene carbonate employed in an amount of from about 85 to about 99.6 weight percent, based on the weight of material within the reaction zone;

(b) providing a catalytic amount of an alkylene oxide carbonation catalyst to said liquid phase, said catalyst a salt characterized by the following formula:

wherein M is potassium or a quaternary ammonium cation of the following formula:

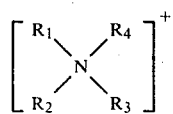

wherein R$_1$, R$_2$, R$_3$ and R$_4$ may each be alkyl, aryl, alkenyl, alkaryl, or aralkyl including substituents thereon in any combination or in which any two or more of the radicals R$_1$, R$_2$, R$_3$ and R$_4$ may be interconnected to form with the basic nitrogen atom a ring of the pyridine, piperidine, quinuclidine, pyrrolidine, pyrroline, morpholine, or thiomorpholine derivatives and 1,4-diazobicyclo[2.2.2]octane, A is bromine, chlorine, or iodine when M is quaternary ammonium cation and is iodine when M is potassium;

(c) having dissolved in said liquid phase sufficient CO$_2$ to provide a molal amount therein which exceeds the molal amount of the catalyst;

(d) providing a CO$_2$ pressure in the reaction zone of between about 150 psig and about 750 psig;

(e) maintaining a sufficient amount of the alkylene oxide in the reaction to maintain the pressure and temperature thereof;

(f) maintaining the reaction zone at a temperature at which the alkylene oxide and CO$_2$ react to form alkylene carbonate, which temperature is not greater than 200° C.; and (g) correlating the reaction zone temperature and pressure to yield an alkylene carbon efficiency of at least about 99% and a conversion of at least about 99.5%.

2. The process of claim 1, wherein the alkylene oxide carbonation catalyst is selected from tetraethylammonium bromide, tetramethylammonium bromide, benzyltriethylammonium bromide, and tetrabutylammonium bromide.

3. The process of claim 1, wherein the alkylene oxide carbonation catalyst is potassium iodide.

4. The process of claim 1, wherein the alkylene oxide carbonation catalyst is utilized in an amount of from 0.1 to about 3.0 weight percent, based on the combined weight of the alkylene carbonate, carbon dioxide and alkylene oxide employed in the reaction zone.

5. The process of claim 4, wherein the catalyst is utilized in an amount of from 0.5 to about 3.0 weight percent.

6. The process of claim 1, wherein the amount of CO$_2$ which is provided in the homogeneous liquid phase mixture comprising the reaction zone is from about 0.1 to about 6 weight percent, based on the weight of the homogeneous liquid phase mixture.

7. The process of claim 1, wherein the pressure in the reaction zone is between about 400 psig and about 750 psig.

8. The process of claim 1, wherein the reaction zone is maintained at a temperature between 100° C. and 200° C.

9. The process of claim 1, wherein the alkylene oxide is ethylene oxide.

10. The process of claim 1, wherein the alkylene oxide is propylene oxide.

11. A process for producing alkylene carbonate by the reaction of carbon dioxide and an alkylene oxide of the formula

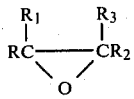

wherein R, $R_1$, $R_2$, and $R_3$ are one or more of hydrogen, alkyl, aryl, alkaryl, aralkyl, cycloalkyl, allyloxy, chloroalkyl, and aryloxy to produce the corresponding alkylene carbonate which comprises:

(a) providing a homogeneous liquid phase reaction zone in which the predominant material therein is the alkylene carbonate, said alkylene carbonate employed in an amount of from about 85 to about 99.6 weight percent, based on the weight of material within the reaction zone;

(b) providing a catalytic amount of an alkylene oxide carbonation catalyst to said liquid phase, said catalyst is selected from tetraethylammonium bromide, tetramethylammonium bromide, benzyltriethylammonium bromide, tetrabutylammonium bromide and potassium iodide;

(c) having dissolved in said liquid phase sufficient $CO_2$ to provide a molal amount therein which exceeds the molal amount of the catalyst;

(d) providing a $CO_2$ pressure in the reaction zone of between about 150 psig and about 750 psig;

(e) maintaining a sufficient amount of the alkylene oxide in the reaction to maintain the pressure and temperature thereof;

(f) maintaining the reaction zone at a temperature at which the alkylene oxide and $CO_2$ react to form alkylene carbonate, which temperature is not greater than 200° C.; and (g) correlating the reaction zone temperature and pressure to yield an alkylene carbonate efficiency of at least about 99% and a conversion of at least about 99.5%.

12. The process of claim 11, wherein the alkylene carbonate is ethylene carbonate.

13. The process of claim 12, wherein the ethylene carbonate produced is such that it can be hydrolyzed to produce ethylene glycol which meets the specifications of Polyester Grade.

* * * * *

UNITED STATES PATENT AND TRADEMARK OFFICE
CERTIFICATE OF CORRECTION

PATENT NO. : 4,214,945
DATED : July 29, 1980
INVENTOR(S) : Malcolm B. Lucas and Robert H. Van Coney It is certified that error appears in the above-identified patent and that said Letters Patent are hereby corrected as shown below:

In the Abstract, line 6, "then" should read --thence--.

In the Abstract, line 19, "Then" should read --Thus,--.

Column 2, line 58, "wherein" should read --therein--.

Column 4, line 45, "now" should read --not--.

Signed and Sealed this

Twenty-fifth Day of November 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,314,945
DATED : February 9, 1982
INVENTOR(S) : C. J. McMullen, et al.

It is certified that error appears in the above—identified patent and that said Letters Patent is hereby corrected as shown below:

Col. 5, line 43, "Huls" should read --Hüls--.

Col. 8, line 14, "greter" should read --greater--.

Signed and Sealed this

Twenty-seventh Day of July 1982

[SEAL]

Attest:

GERALD J. MOSSINGHOFF

Attesting Officer    Commissioner of Patents and Trademarks